US00PP35381P2

(12) United States Plant Patent
Van Swieten

(10) Patent No.: US PP35,381 P2
(45) Date of Patent: Sep. 12, 2023

(54) ***PHALAENOPSIS* ORCHID PLANT NAMED 'PHA773779'**

(50) Latin Name: ***Phalaenopsis* hybrid**
Varietal Denomination: PHA773779

(71) Applicant: ANTHURA B.V., Bleiswijk (NL)

(72) Inventor: Martinus Nicolaas Gerardus Van Swieten, Utrecht (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/804,000

(22) Filed: Feb. 23, 2023

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — Jondle & Associates, P.C.

(57) ABSTRACT

A new and distinct variety of *Phalaenopsis* plant named 'PHA773779', particularly characterized by having white flowers with greenish-yellow and white lips, flowers that are concave in lateral view, lip curvature of lateral lobe is medium, and semi-erect to horizontal leaf attitude, is disclosed.

3 Drawing Sheets

Genus and species: *Phalaenopsis* hybrid.
Variety denomination: 'PHA773779'.

BACKGROUND OF THE NEW PLANT

The present invention relates to a new and distinct cultivar of *Phalaenopsis* plant, botanically known as *Phalaenopsis* hybrid of the Orchidaceae family, commonly referred to as moth orchid, and hereinafter referred to by the variety name 'PHA773779'.

The new *Phalaenopsis* plant is a product of a planned breeding program conducted by the inventor in Bleiswijk, the Netherlands. The objective of this breeding program was to create a new *Phalaenopsis* plant with numerous attractive white flowers with greenish-yellow and white lips, suitable for potted plant production.

The new *Phalaenopsis* plant 'PHA773779' is a result of cross-pollination made by the inventor in January 2014 in Bleiswijk, the Netherlands, of the proprietary female, or seed parent, *Phalaenopsis* hybrid '07-023312-0004' (unpatented) with the proprietary male, or pollen parent, *Phalaenopsis* hybrid 'PHALDIPWEQ' (U.S. Plant Pat. No. 26,466).

The new *Phalaenopsis* was selected by the inventor as a single plant within the progeny of the stated cross-pollination in a controlled greenhouse in Bleiswijk, the Netherlands, in October 2016. Asexual reproduction of the new *Phalaenopsis* plant by meristem tissue culture since 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Apr. 22, 2021 (Application no. 2021/1105), by Applicant who obtained the subject matter disclosed directly from the inventor. 'PHA773779' has not been made publicly available or sold anywhere in the world prior to the effective filing date of this application with the exception of sales or disclosures made one year or less before the effective filing date of this claimed invention by Applicant who obtained 'PHA773779' directly from the inventor.

SUMMARY OF THE INVENTION

The following are the most outstanding and distinguishing characteristics of this new cultivar when grown under normal horticultural practices in Bleiswijk, the Netherlands, and can be used to distinguish 'PHA773779' as a new and distinct variety of *Phalaenopsis* plant:

1) White flowers with greenish-yellow and white lips;
2) Flower shape in lateral view is concave;
3) Lips: curvature of, lateral lobe is medium; and
4) Leaf attitude is semi-erect to horizontal.

DESCRIPTION OF THE PHOTOGRAPHS

This new *Phalaenopsis* plant is illustrated by the accompanying photographs which show the overall plant habit including blooms, buds, and foliage of the plant; the colors shown are as true as can be reasonably obtained by conventional photographic procedures. The photographs were taken in a greenhouse in Bleiswijk, the Netherlands, from 50-week-old plants in September 2022. Colors in the photographs may differ from the color values cited in the detailed botanical description, which accurately describe the actual colors of the new variety.

DESCRIPTION OF THE NEW VARIETY

Figure 1:
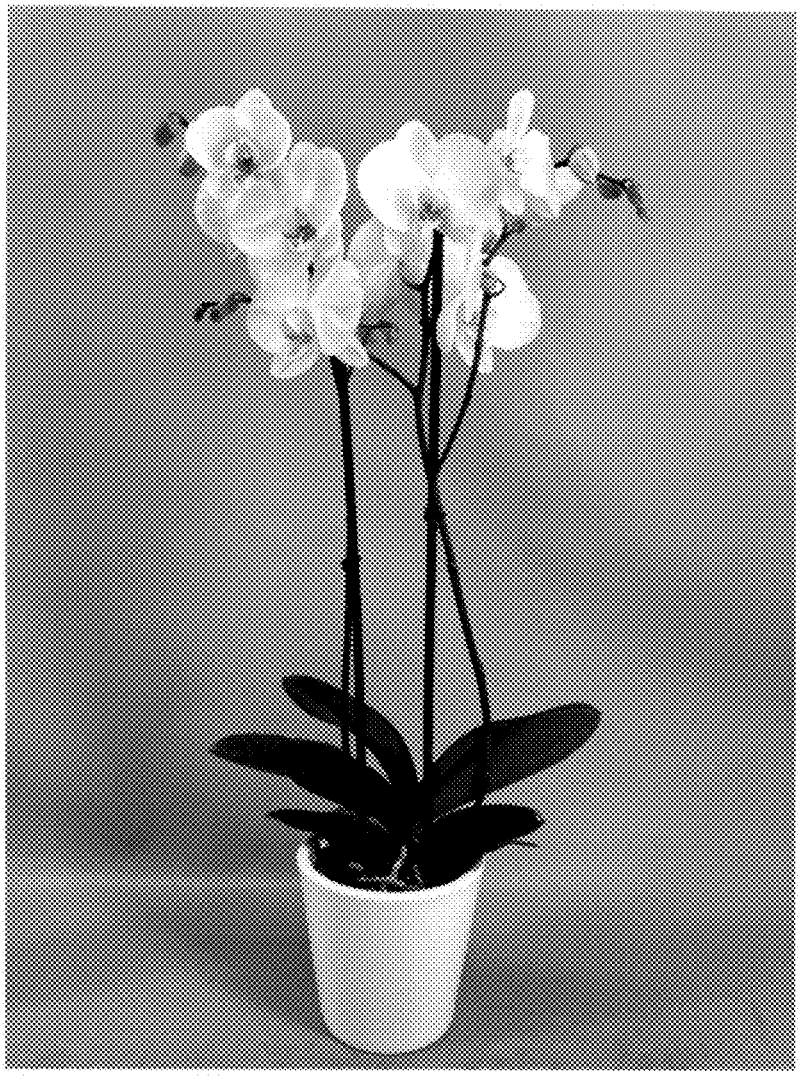
FIG. 1 shows the overall plant habit, including blooms, buds, and foliage of 'PHA773779'.
Figure 2:
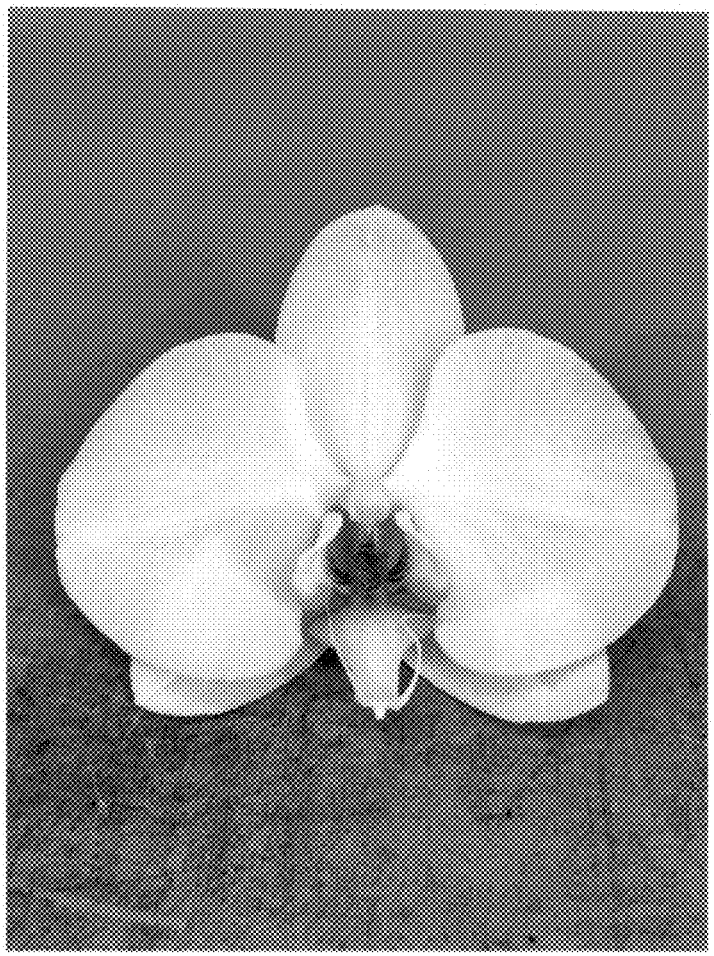
FIG. 2 shows a close-up of a flower of 'PHA773779'.
Figure 3:
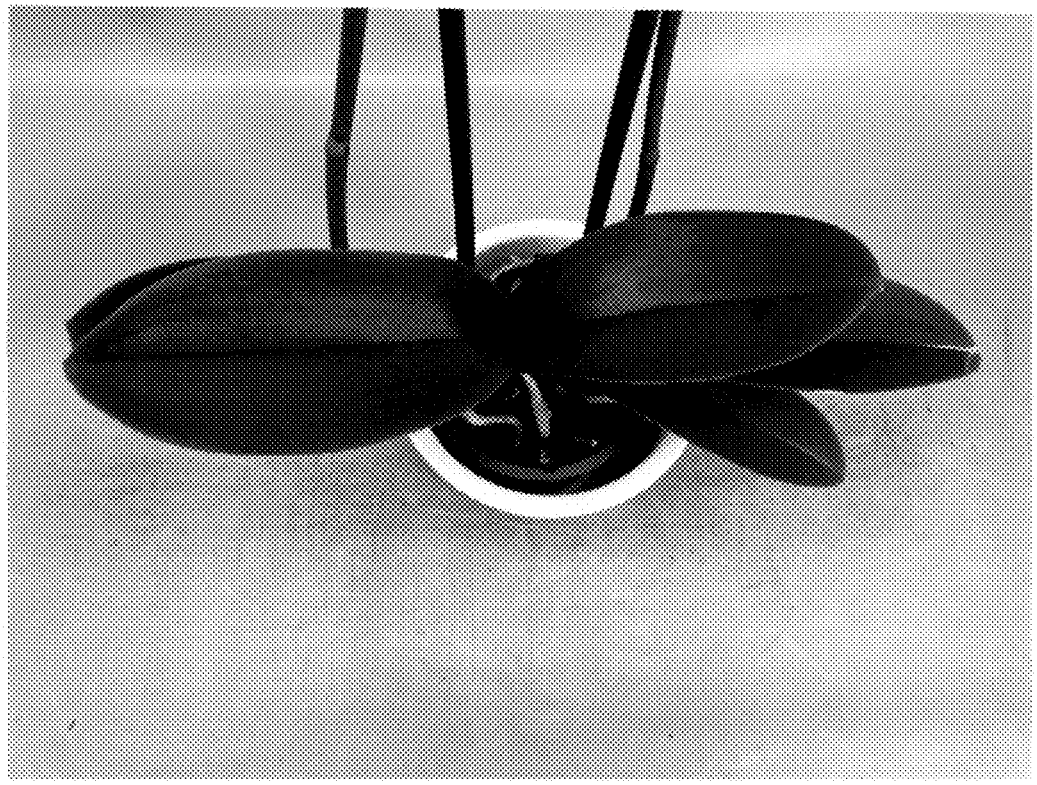
FIG. 3 shows an overhead view of the leaves of 'PHA773779'.

The following detailed description sets forth the distinctive characteristics of 'PHA773779'. Plants of the new

*Phalaenopsis* have not been observed under all possible environmental conditions. The phenotype may vary somewhat with variations in environment such as temperature, light intensity, and day length, without, however, any variance in genotype. The chart used in the identification of colors described herein is The R.H.S. Colour Chart of The Royal Horticultural Society, London, England, 2015 edition, except where general color terms of ordinary significance are used. The color values were determined under 4000-6000 lux natural light in a greenhouse in Bleiswijk, the Netherlands. Observations and measurements were made in September 2022 on flowering plants which were planted in 12-centimeter (diameter) pots. After in vitro propagation, the plants were grown in nursery trays for 20 to 24 weeks, followed by transplantation into 12-centimeter (diameter) pots and grown in a greenhouse between 27° C. to 29° C. for 30 weeks, continued by a cooling period of 8 weeks between 18° C. to 20° C. and 12 weeks in a greenhouse of 21° C. Flowering occurs after 50 weeks in 12-centimeter pots.

DETAILED BOTANICAL DESCRIPTION

Classification:

*Family.*—Orchidaceae.

*Botanical.*—*Phalaenopsis* hybrid.

*Common name.*—Moth orchid.

*Variety name.*—'PHA773779'.

Parentage:

*Female parent.*—*Phalaenopsis* cultivar '07-023312-0004' (unpatented).

*Male parent.*—*Phalaenopsis* cultivar 'PHALDIPWEQ' (U.S. Plant Pat. No. 26,466).

Propagation:

*Type.*—Meristem tissue culture.

Roots:

*Root description.*—Greyed-green (a color in between RHS 190B and RHS 190C) colored roots with branching lateral roots having yellow-green (RHS 144C) colored root tips.

Plant:

*Crop time to flowering.*—Following asexual propagation (in vitro), the rooted cuttings grow for 20 to 24 weeks. After transplantation into 12-cm pots, the plant is finished after 48 to 50 weeks.

*Growth habit of the peduncle.*—Upright to slightly pendent with panicle inflorescence.

*Height* (*from soil level to top of inflorescence*).—Approximately 58.0 cm to 63.0 cm.

*Width* (*measured from leaf tips*).—About 34.0 cm to 36.0 cm.

*Vigor.*—Strong.

Leaves:

*Mature leaves.*—Quantity per plant: 9 to 10 leaves are produced before flowering. Length (fully expanded): 16.0 cm to 18.0 cm. Width: 6.5 cm to 7.5 cm. Position of the broadest part of the leaf: At the middle. Shape: Oblong. Base shape: Moderately elongated. Apex: Slightly asymmetric. Leaf blade angle with the petiole (measured from the horizontal position): Between 20 degrees and 30 degrees. Leaf margin: Entire. Color: Upper surface: RHS 147A. Lower surface: RHS 146A. Texture (both upper and lower surfaces): Smooth. Thickness: 2.0 mm to 3.0 mm. Variegation: Absent. Venation: Pattern: Parallel. Color of the midvein: Upper surface: RHS 147A. Lower surface: RHS 146A.

Peduncle:

*Quantity per plant.*—1 to 2.

*Number of flowers per peduncle.*—13 to 18.

*Length.*—58.0 cm to 63.0 cm.

*Diameter.*—5.0 mm to 7.0 mm.

*Strength.*—Strong.

*Aspect.*—Upright to slightly pendent.

*Texture.*—Smooth.

*Color.*—Mix of yellow-green (RHS 146C) and reddish-brown (RHS 200B).

*Internode length.*—3.0 cm to 4.0 cm.

Inflorescence description:

*Appearance.*—Upright to slightly pendent, panicle inflorescence with bilaterally symmetrical flowers that open in succession beginning with the lowermost flower.

*Number of inflorescences.*—1 to 2.

*Inflorescence size.*—Height (from base to tip): 240.0 mm to 340.0 mm.

*Flowering time.*—First flowers can be expected 10 to 11 months after planting in a 12-cm pot.

*Flower.*—Height: 85.0 mm to 90.0 mm. Diameter: 100.0 mm to 105.0 mm. Depth of lip: 30.0 mm to 32.0 mm.

*Flower shape.*—Concave.

*Flower longevity.*—On the plant: 9 to 11 weeks.

*Fragrance.*—Absent.

*Flower bud.*—Average size: Large. Length: 24.0 mm to 26.0 mm. Width: 18.0 mm to 20.0 mm. Shape: Egg shaped. Color: Light yellow-green (RHS 145C) with a touch of purple shade (RHS 77D).

*Petals.*—Arrangement: Open/free. Shape: Semi-circular. Apex: Slightly asymmetric. Margin: Entire. Length (from base to tip): 49.0 mm to 51.0 mm. Width: 61.0 mm to 63.0 mm. Position of the broadest part of the petal: Toward the base. Color (when fully opened): Upper surface: Basic color: White (RHS NN155C). Over color: Absent. Lower surface: Basic color: White (RHS NN155C). Over color: Light reddish-purple midvein (RHS N78D). Number of spots and stripes on the petals (upper surface): None. Color of spots and stripes on the petals (upper surface): Not applicable. Density of netting of the petals (upper surface): None. Color of the netting (upper surface): Not applicable.

*Dorsal sepal.*—Shape: Elliptic. Apex: Obtuse symmetric. Margin: Entire. Length (from base to tip): 50.0 mm to 52.0 mm. Width: 35.0 mm to 37.0 mm. Position of the broadest part of the dorsal sepals: At the middle. Color (when fully opened): Upper surface: Basic color: White (RHS NN155C). Over color: Absent. Lower surface: Basic color: White (RHS NN155C). Over color: Light yellowish-green (RHS 157C) at the middle from the base toward the tips and very light purple shade (RHS 76B). Number of spots and stripes on the dorsal sepals (upper surface): None. Color of spots and stripes on the dorsal sepals (upper surface): Not applicable. Density of netting of the dorsal sepals (upper surface): None. Color of the netting: Not applicable.

*Lateral sepals.*—Shape: Ovate. Apex: Obtuse asymmetric. Margin: Entire. Length (from base to tip): 52.0 mm to 54.0 mm. Width: 28.0 mm to 30.0 mm.

Position of the broadest part of the lateral sepals: Toward the base. Color (when fully opened): Upper surface: Basic color: White (RHS NN155C). Over color: Touch of light yellow-green (RHS 145D). Lower surface: Basic color: White (RHS NN155C). Over color: Light yellow-green (RHS 157A); touch of very light purple (RHS 76C) toward margins and light reddish-purple midvein (RHS N78D) toward tips. Number of spots and stripes on the lateral sepals (upper surface): None. Color of spots and stripes on the lateral sepals (upper surface): Not applicable. Density of netting of the lateral sepals (upper surface): None. Color of the netting (upper surface): Not applicable.

*Labellum* (*lip*).—Whiskers: Present. Length of whiskers: 28.0 mm to 30.0 mm. Color of whiskers: White (RHS NN155C) with light greenish-yellow tips (RHS 2C). Pubescence on the lip: Absent.

*Lateral lobe.*—Shape: Type V (as described in the International Union for the Protection of New Varieties of Plants (UPOV) Test Guidelines for *Phalaenopsis*); spatulate. Margin: Medium undulated. Length: 21.0 mm to 23.0 mm. Width: 14.0 mm to 16.0 mm. Color: Upper surface: Touch of light yellow (RHS 11B) and striped at the base RHS 176B; greenish-yellow (RHS 153B) toward margin on one side; white (RHS NN155C) toward the tips. Lower surface: Greenish-yellow (RHS 8D) toward the margin on one side; white (RHS NN155C) toward margin on one side and tips. Number of spots and stripes on the lateral lobe: Few to medium stripes. Color of spots and stripes on the lateral lobe: RHS 176B. Density of netting of the lateral lobe: None. Color of the netting: None.

*Apical lobe.*—Shape: Triangular. Margin: Entire. Length: 23.0 mm to 25.0 mm. Width: 22.0 mm to 24.0 mm. Color: Upper surface: Reddish-orange (RHS 176C) margin and greenish-yellow (RHS 151C) at the base; white (RHS NN155C) toward the whiskers. Lower surface: Reddish-orange (RHS 176C) margin and greenish-yellow (RHS 151C) at the base; white (RHS NN155C) toward whiskers. Number of spots and stripes on the apical lobe: None. Color of spots and stripes on the apical lobe: Not applicable. Density of netting of the apical lobe: None. Color of the netting: None applicable.

*Callus.*—Average size: Medium to large. Height: 8.0 mm to 9.0 mm. Length: 6.0 mm to 7.0 mm. Width: 5.0 mm to 6.0 mm. Color: Orange (RHS 178B) toward tips; yellow (RHS 12B) on sides; dotted RHS 178B.

Reproductive organs:

*Column.*—Length: 10.0 mm to 11.0 mm. Diameter: 6.0 mm to 7.0 mm. Color: White (RHS NN155C).

*Pollinia.*—Quantity: 2. Diameter: 0.8 mm to 1.0 mm. Color: Orange-yellow (RHS 23A).

*Ovary.*—Length: 13.0 mm to 16.0 mm. Diameter: 2.2 mm to 2.6 mm.

*Pedicel.*—Length: 37.0 mm to 40.0 mm. Diameter: 2.7 mm to 3.0 mm. Color: Yellow-green (RHS 146C) at the base; light yellow-green (RHS 145C) with a touch of very light purple (RHS 76B) toward the flower. Texture: Smooth.

Disease, pest, and stress resistance: No specific resistance or susceptibility observed to pathogens and pests common to *Phalaenopsis* to date.

Fruit and seeds: Fruit and seed development has not been observed on plants of the new *Phalaenopsis* to date.

COMPARISON WITH PARENTAL LINES AND MOST SIMILAR VARIETIES

'PHA773779' differs from the female parent plant '07-023312-0004' (unpatented) in that 'PHA773779' has larger flowers and semi-erect to horizontal leaf attitude, whereas '07-023312-0004' has smaller flowers and horizontal leaf attitude.

The male parent plant of 'PHA773779', 'PHALDIPWEQ' (U.S. Plant Pat. No. 26,466), is no longer in existence, therefore a meaningful comparison cannot be made.

'PHA773779' is most similar to the commercial *Phalaenopsis* plants named 'PHALHOQGAI' (U.S. Plant Pat. No. 33,571) and 'PHALHORDIN' (U.S. Plant Pat. No. 33,096). 'PHA773779' differs from the commercial variety 'PHALHOQGAI' in that 'PHA773779' has larger flowers, wider leaves, and medium curvature of lateral lobe lips, whereas 'PHALHOQGAI' has smaller flowers, more narrow leaf width, and strong curvature of lateral lobe lips. Additionally, 'PHA773779' has longer whiskers than 'PHALHOQGAI'.

'PHA773779' differs from the commercial variety 'PHALHORDIN' in that 'PHA773779' has larger, concave flowers in lateral view, and longer whiskers, whereas 'PHALHORDIN' has smaller, flat flowers in lateral view, and shorter whiskers.

I claim:

1. A new and distinct variety of *Phalaenopsis* plant named 'PHA773779', substantially as described and illustrated herein.

* * * * *